United States Patent [19]

Wu

[11] 4,160,696

[45] Jul. 10, 1979

[54] ASCORBIC ACID DETERMINATION

[75] Inventor: Tai-Wing Wu, Rochester, N.Y.

[73] Assignee: Eastman Kodak Company, Rochester, N.Y.

[21] Appl. No.: 716,921

[22] Filed: Aug. 23, 1976

[51] Int. Cl.$^2$ ............................................. G01N 31/14
[52] U.S. Cl. ...................................................... 435/25
[58] Field of Search .................... 195/99, 103.5 R, 63, 195/127; 426/231

[56] References Cited

U.S. PATENT DOCUMENTS 3,992,158  11/1976  Przybylowicz ............... 195/103.5 R

OTHER PUBLICATIONS

Deutsch et al., J. of the A.O.A.C., vol. 48, No. 6, 1965, pp. 1248–1256.
Archibald, J. Biol. Chem. 158, (1945), pp. 347–373.

Primary Examiner—David M. Naff
Attorney, Agent, or Firm—Arthur H. Rosenstein

[57] ABSTRACT

Ascorbic acid in a sample such as blood serum is quantitatively assayed by converting the ascorbic acid to dehydroascorbic acid with ascorbic acid oxidase and reacting the dehydroascorbic with a coupling substance such as phenylenediamine to produce a detectable product. The ascorbic acid oxidase and coupling substance can be combined to form a reagent composition which can be incorporated into integral multilayer elements to form a test element.

19 Claims, 1 Drawing Figure

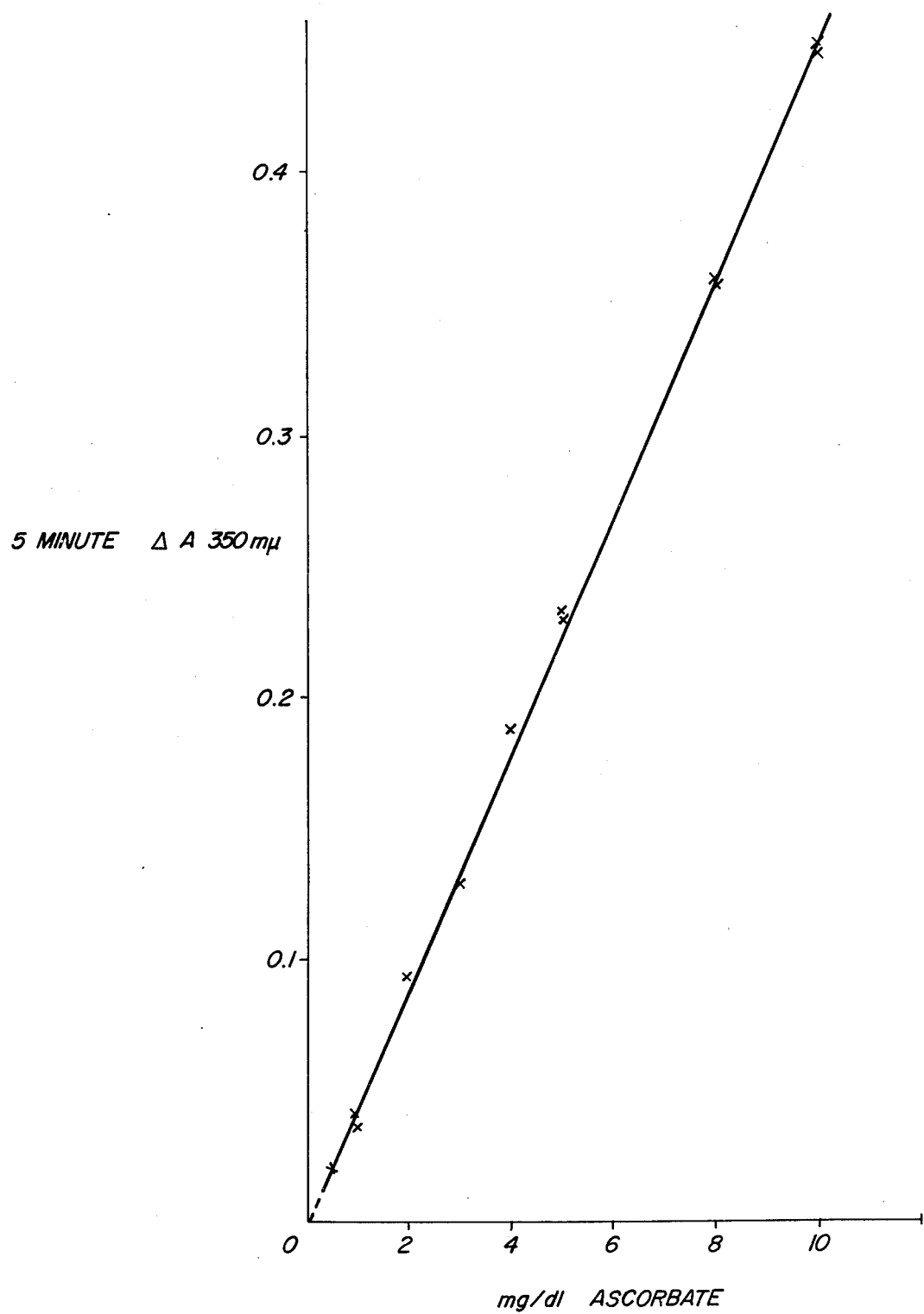

ASCORBIC ACID DETERMINATION

BACKGROUND OF THE INVENTION

1. Field of the Invention

The present invention relates to a method and composition for the determination of ascorbic acid in aqueous liquids.

2. Description of the Related Art

Ascorbic acid is essential for the normal regulation of the colloidal conditions of intracellular substances, including the fibrils and collagen of connective tissues. Deficiency of Vitamin C (i.e., ascorbic acid) results in abnormal development and maintainence of tissue structures, capillary defects, and eventual development of scurvy. There is, therefore, a need for determining ascorbic acid in body fluids.

Methods and techniques for assaying ascorbic acid are comprehensively reviewed in Rae, J. H., Methods Biochem. Analy. 1, p. 115, 1960 and Henry, R. J., Connor, D. C., and Winkleman, J. W., Clinical Chemistry, Principles and Technics, Second Edition, Harper and Row, 1964, p. 1394. The most commonly used early method involves titration with an oxidation-reduction indicator such as 2,6-dichlorophenolindophenol in acid solution.

Some of the more recent adaptations and approaches to the determination of ascorbic acid are the reduction of mercuric to mercurous chloride by urinary ascorbic acid (Kum-Tatt, L., Leong, P. C., Clin. Chem. 10, p. 575, 1964), resin extraction of urinary ascorbic acid and measurement by 2,6-dichlorindophenol (Hughes, R. E., Analyst, 89, p. 618, 1964), reduction of ferric to ferrous ion and photometric measurement with bathophenanthroline (Vann, L. S., Clin. Chem., 11, p. 979, 1965), reaction with diazotized 4-nitroaniline-2,5-dimethoxyaniline (Michaëlsson, G., Michaëlsson, M., Scand. J. Clin. Lab. Invest., 20, p. 97, 1967), oxidation of ascorbic acid with 2,6-dichloroindophenol followed by formation of hydrazones (Pelletier, O., J. Lab. Clin. Med., 72, p. 674, 1968), and the reduction of 1,2-naphthoquinone by ascorbic acid to the fluorescent dihydro derivative (Hubmann, B., Monnier, D., Roth, M., Clin. Chim. Acta., 25, p. 161, 1969). Two automated methods have been described. One such method utilizes the production of a dichloroindophenol dye (Garry, P. J., Owen, G. M. Technicon Symp. 1, p. 507, 1967), and the other the 4-methoxy-2-nitroaniline reaction (Wilson, S. S., Guillan, R. A., Clin. Chem., 15, p. 282, 1969).

Most if not all of these prior art techniques are undesirable from two standpoints. First, the selectivity of the various methods has been doubtful because of the relative specificity of the reagents used and the potential that other components of a complex liquid under analysis might be interfering. Second, these methods generally require some or all of the following: extended reaction periods, high degree of technician participation or heating the liquid under analysis to excessively high temperatures on the order of 50°-60° C. which can yield distorted results.

Deutsch, M. J. and Weeks, C. E., Journal of the A.O.A.C. 48, No. 6, 1965, p. 1248 describe the assay of ascorbic acid in foods and vitamin pills using the reaction of o-phenylenediamine with dehydroascorbic acid to form a fluorescent quinoxaline. The dehydroascorbic acid is obtained by treating ascorbic acid with purified charcoal from birch.

There is no suggestion in any of the foregoing publications that the ascorbic acid oxidase interaction can be coupled to the dehydroascorbic acid detection system described by Deutsch et al to yield a highly specific technique for determining ascorbic acid.

RELATED APPLICATION

A related application is concurrently filed U.S. patent application Ser. No. 716,919, filed Aug. 23, 1976, now abandoned, of Wu et al, entitled Reduction of Ascorbic Acid Interference in Assays of Aqueous Fluids.

DESCRIPTION OF THE DRAWING

FIG. 1 is a graph of replicate ascorbate determinations obtained at various levels of ascorbate at a five minute endpoint using the methods and compositions described herein.

SUMMARY OF THE INVENTION

We have now developed a novel method for the assay of ascorbic acid in aqueous liquids such as blood serum which is highly selective (based on an enzyme reaction), very rapid (requires less than 5 minutes), and can be carried out at relatively low temperatures (below or about 37° C.).

This method involves contacting in an aqueous medium a sample for analysis and a novel assay composition comprising ascorbic acid oxidase which catalyzes conversion of the ascorbic acid to dehydroascorbic acid, reaction of the latter compound with a coupler to produce a detectable product and detecting the detectable product. This method permits the quantitative determination of ascorbic acid in biological liquids such as blood serum.

DESCRIPTION OF THE PREFERRED EMBODIMENTS

The terms ascorbic acid and ascorbate are used interchangeably herein to refer to both ascorbic acid present in its free form as a carboxylic acid and in its combined form as an ascorbate ester when combined with various hydroxyl containing compounds present in liquid under analysis.

The present invention couples the enzymatic conversion of L-ascorbate to dehydroascorbate by ascorbate oxidase and the reaction of dehydroascorbate with certain coupling substances to produce a detectable product, preferably in proportion to the amount of ascorbic acid (ascorbate) contained in a liquid sample contacted with the assay composition.

Ascorbate oxidase (L-Ascorbate:oxygen oxidoreductase, 1.10.3.3) (hereinafter identified as ASO) is known in the art. This enzyme catalyzes the reaction

$$2\text{L-ascorbate} + O_2 \rightarrow 2 \text{ dehydroascorbate} + 2H_2O.$$

So long as the enzyme catalyzes the foregoing conversion and does not generate products which interfere with the subsequent coupling of the dehydroascorbate according to the reaction dehydroascorbate + coupling substance → detectable product, the particular enzyme or its source is not critical.

An enzyme extracted from *Cucurbita pepo medullosa* using the technique described in Tables I and II below is particularly useful in the compositions and methods described herein. This enzyme has a pH optimum between about 5.7 and about 8.7 and hence assay compositions and media for the detection/determination of ascorbic acid using these methods and materials are buffered in a conventional fashion at this level. Particularly useful buffers include Tris-HCl$_2$, Na+ and K+ phosphates, Tris-phosphate, Tris ($10^{-4}$ M EDTA)-all at or about 0.05M. Most preferred is sodium phosphate.

It is preferred, in order to optimize the assay, to buffer the composition at a substantially neutral pH, i.e., between about 6.8 and 7.2 and most preferred to buffer between about 6.8 and 7.0.

The ASO extraction technique described below produces an extract which demonstrates a specific activity of about 3.0–5.5 I.U. per mg of protein. One unit of enzyme activity is defined as that amount of enzyme protein which will oxidize 1 μmole of ascorbate per minute in 0.05M sodium phosphate buffer at 37° C. and pH 6.80+0.05.

Table I

Purification Protocol fo Ascorbate Oxidase from Zucchini Squash (Cucurbita pepo medullosa)

Green Squash (6–8 lbs) briefly rinsed with distilled water
↓
Peelings homogenized in 2–3 volumes of P$_i$ buffer (0.05M sodium phosphate at pH 6.8) (pulp discarded)
↓
Homogenate squeezed through 2–3 layers of cheesecloth
↓
Filtrate centrifuged (4080 × g, 15 minutes) to remove cell debris and insoluble material
↓
Solution (supernatant) adjusted to 65% saturation with respect to (NH$_4$)$_2$SO$_4$, stirred for 1 hr in cold (0° C.), stood ½ hr in cold pellet resuspended in P$_i$ buffer    supernatant discarded
↓
ice-cold acetone (0.9 volume of enzyme solution) added with stirring
↓
22,450 × g, 30 minutes
↓
Pellet resuspended in P$_i$ buffer (minimal volume)
↓
Dialyzed against 2–3 changes of P$_i$ buffer
↓
Centrifugation to remove insoluble material (slow spin)
↓
Ready to use or stored at −20° C. (stable for months)

Table II

Summary of Purification of Ascorbate Oxidase

| Step | | Preparation | Total mg protein | Specific Activity (Units/mg) | Total Units | Activity Recovery (%) | Apparent Purification Factor |
|---|---|---|---|---|---|---|---|
| 1. | Crude homogenate of peelings | A | 2800 | 0.67 | 1876 | 100 | 1 |
|    |                              | B | 12800 | 0.89 | 11392 | 100 | 1 |
| 2. | Ammonium Sulfate Precipitation | A | 2150 | 0.82 | 1760 | 94 | 1.22 |
|    |                                 | B | 6042 | 1.71 | 10331 | 91 | 1.92 |
| 3. | Acetone Precipitation | A | 1278 | 0.89 | 1137 | 61 | 1.33 |
|    |                        | B | 5130 | 1.61 | 8259 | 72 | 1.81 |
| 4. | Dialysis | A | 243 | 3.4 | 826 | 44 | 5.1 |

Table II- Continued

Summary of Purification of Ascorbate Oxidase

| Step | Preparation | Total mg protein | Specific Activity (Units/mg) | Total Units | Activity Recovery (%) | Apparent Purification Factor |
|------|-------------|------------------|------------------------------|-------------|----------------------|------------------------------|
|      | B           | 549              | 5.6                          | 3074        | 27                   | 6.3                          |

Important Notes:
These two preparations started from 3.2 kg of purchased Zucchini squash. The actual dry weight of each praparation after lyophilization of the dialysate was approximately 2 to 3 times the gram weight as determined by the procedure of Lowry. Thus, preparation (A) yielded a dry weight of ~0.69 grams while (B) 1.7 grams. It is this dry weight which is quoted in this work.

The second critical component of the assay compositions hereof comprises a substance, compound or material which couples i.e., interacts with the dehydroascorbic acid to form a detectable product, preferably a colored or fluorescent product in proportion to the amount of ascorbic acid/ascorbate contained in a sample under analysis. Thus, substantially any coupling substance so interactive in a medium which permits analysis of ascorbic acid/ascorbate by ASO is considered useful in the successful practice of the instant invention.

Such coupling substances include by way of example, o-, m- and p-phenylenediamines substituted or unsubstituted which combine with dehydroascorbic acid to yield a blue fluorophor, which can be monitored spectrophotometrically or fluorometrically. o-Phenylenediamine is specifically preferred from among this group of couplers. Certain of these coupling substances perform more satisfactorily in the presence of small amounts of organic solvents such as methanol which appear to impart increased solubility.

Other examples of useful such materials are:
N,N-dimethyl p-phenylenediamine dihydrochloride
N,N-dimethyl p-phenylenediamine monohydrochloride
2,3,5,6-tetramethyl p-phenylenediamine dihydrochloride hydroquinone
2,4-diaminophenol dihydrochloride
4-amino-N-ethyl-N-($\beta$-methylsulfonamidoethyl)-m-toluidine sesquesulfate monohydrate
p-aminophenol monohydrochloride
N-ethyl-N-($\beta$-hydroxyethyl)-p-phenylenediamine sulfate p-phenylenediamine dihydrochloride A useful composition thus comprises ascorbic acid oxidase, buffer and a coupling substance. Such a composition can be provided either as a dry mixture of lyophilized enzyme and powdered buffer and coupler readily reconstitutable with water or an aqueous solution. Furthermore, assay compositions as described herein can be incorporated into any of the wide variety of test elements well known to those skilled in the art. Such elements generally comprise an absorbent matrix, for example paper, impregnated with reagents. Typical such materials and elements produced therewith which can be adapted for the assay of ascorbic acid using the compositions described herein are those described, for example, in the following U.S. patents: U.S. Pat. Nos. 3,092,465, 3,418,099, 3,418,083, 2,893,843, 2,893,844, 2,912,309, 3,008,879, 3,802,842, 3,798,064, 3,298,739, 3,915,647, 3,917,453, 3,933,594, 3,936,357, etc.

Such compositions can also be incorporated into multilayer analytical elements of the type described in Belgian Pat. No. 801,742 published Jan. 2, 1974 and U.S. Pat. No. 3,992,158 issued Nov. 16, 1976. A more detailed discussion of useful such elements is presented below.

In whatever physical state the reagent composition is initially provided it should be such as to produce, at the time of use, an aqueous medium comprising at least about 10μg/ml of ASO, from about $5 \times 10^{-3}$ to about $10^{-2}$M coupling substance and sufficient buffer to provide a pH of between about 5.7 and about 8.7, preferably between about 6.8 and 7.2 and most preferably between about 6.8 and 7.0. Lowering of the coupling substance concentration below this range reduces the dynamic range of the test rather significantly. However, coupling substance levels below this range may be useful for qualitative ascorbic acid detection. Although the determination can be carried out at temperatures of between about 16 and 40° C., best results are obtained at a temperature of 20°±2° C. The time required for any given determination will, of course, vary depending upon the particular reagents used, the concentration of reagents and the temperature of the determination. Using the preferred materials and conditions, optimum results are obtained in about 5 minutes.

As alluded to hereinabove, the compositions described herein can be incorporated into single- or multilayered analytical elements of the type described in the extensive prior art in this field.

It is preferred to incorporate the compositions described herein into analytical elements of the type described in aforementioned Belgian Patent No. 801,742 published January 2, 1974.

According to a highly preferred embodiment, elements for the determination of ascorbic acid comprise:

1. a spreading layer which serves to deliver a uniform apparent concentration of ascorbic acid contained in a sample applied thereto to;

2. a reagent layer comprising at least a portion of the assay composition described hereinabove and in fluid contact with the spreading layer under conditions of use.

Optionally, the element may also include an indicator layer which contains material which interacts with dehydroascorbic acid to produce a detectable product.

Reference herein to fluid contact between layers in an analytical element identifies the ability of a fluid, whether liquid or gaseous, to pass in such element between superposed regions of a spreading layer and a reagent layer or other layers in fluid contact. Stated in another manner, fluid contact refers to the ability to transport components of a fluid between the layers in fluid contact. Although such layers in fluid contact can be contiguous, they may also be separated by intervening layers as described in detail hereinafter. However, layers in the element that physically intervene layers in mutual fluid contact will not prevent the passage of fluid between the fluid contacting layers.

The Spreading Layer

As used herein, the term spreading layer refers to a layer, isotropically porous or otherwise, that can accept a liquid sample, whether applied directly to the spreading layer or provided to it from a layer or layers in fluid contact with the spreading layer, and within the layer distribute (i.e., meter) the solvent or dispersion medium of the sample and at least one dissolved or dispersed component such that a uniform apparent concentration of such component is provided at the surface of the spreading layer facing the reagent layer(s) of the element. It should be understood that the uniformity of such concentration is a perceived uniformity as measured by techniques like those described hereinafter. (The spreading layer is synonymously referred to herein as the metering layer.) In the context of this invention, spread sample components will, of course, include ascorbic acid or ascorbic acid esters which may be present in the applied sample. It will be appreciated that such an apparent concentration can be achieved with concentration gradients present through the thickness of, or otherwise in, the spreading layer. Such gradients do not present any difficulty to obtaining quantitative test results if they are not detectable during result measurement or can be accommodated using known calibration techniques.

The spreading layer can be an isotropically porous layer. Reference herein to isotropic porosity identifies the fact of substantial porosity in all directions within the spreading layer. It will be understood that the degree of such porosity may be variable, if necessary or desirable, for example, regarding pore size, percentage of void volume or otherwise. It shall be understood that the term isotropic porosity (or isotropically porous) as used herein should not be confused with the terms isoporous or ionotropic often used with reference to filter membranes to signify those membranes having pores that are continuous between membrane surfaces. Likewise, isotropic porosity should not be confused with the term isotropic, used in contradistinction to the term anisotropic, which signifies filter membranes having a thin "skin" along at least one surface of the membrane. See, for example, *Membrane Science and Technology*, James Flinn Ed, Plenum Press, New York (1970).

As will be appreciated, the extent of spreading is dependent in part on the volume of liquid to be spread. However, it should be emphasized that the uniform apparent concentration obtained with spreading is substantially independent of liquid sample volume and will occur irrespective of the extent of spreading. As a result, elements of this invention generally do not require precise sample application techniques. However, a particular liquid sample volume may be desirable for reasons of preferred spread times or the like. Because the elements of this invention are able to produce quantitative results using very small sample volumes that can be entirely taken up within a conveniently sized region of the spreading layer (e.g., one square centimeter), there is no need to remove excess moisture from the element after application of a liquid sample. Further, because spreading occurs in the spreading layer and the spread component is provided to the fluid contacting reagent layer without apparent substantial lateral hydrostatic pressure, there is not the "ringing" problem often seen with prior analytical elements when soluble reagents were used.

The spreading layer need only produce a uniform apparent concentration of spread component per unit area at its surface facing a reagent layer with which the spreading layer is in fluid contact, and it is very convenient to determine whether a particular layer can be suitable for spreading purposes by means of the simple test described in the aforementioned Przybylowicz and Millikan application Ser. No. 538,072, now U.S. Pat. No. 3,992,158, and incorporated herein by reference.

Isotropically porous layers can be prepared using a variety of components. In one aspect, particulate material can be used to form such layers, wherein the isotropic porosity is created by interconnected spaces between the particles. Various types of particulate matter, all desirably chemically inert to sample components under analysis, are useful. Pigments, such as titanium dioxide, barium sulfate, zinc oxide, lead oxide, etc., are desirable. Other desirable particles are diatomaceous earth and microcrystalline colloidal materials derived from natural or synthetic polymers. Such microcrystalline materials are described in an article entitled "Colloidal Macromolecular Phenomena, Part II, Novel Microcrystals of Polymers" by O. A. Battista et al published in the *Journal of Applied Polymer Science*, Vol. II, pages 481–498 (1967). Microcrystalline cellulose, which is commercially available from FMC Corporation under the name Avicel, is an example of such a colloidal material which is satisfactory for use in the present invention. Spherical particles of uniform size or sizes, such as resinous or glass beads, can also be used and may be particularly desirable where uniform pores are advantageous, such as for selective filtration purposes. If a particulate material of choice is not adherent, as in the case of glass beads or the like, it can be treated to obtain particles that can adhere to each other at points of contact and thereby facilitate formation of an isotropically porous layer. As an example of suitable treatment, non adherent particles can be coated with a thin adherent layer, such as a solution of hydrophilic colloid like gelatin or polyvinyl alcohol, and brought into mutual contact in a layer. When the colloid (i.e., binder) coating dries, the layer integrity is maintained and open spaces remain between its component particles.

As an alternative or in addition to such particulate materials, the spreading layer can be prepared using an isotropically porous continuous polymer phase. It is possible to prepare such polymers using techniques useful in forming "blush" polymers. "Blush" polymer layers can be formed on a substrate by dissolving a polymer in a mixture of two liquids, one of which is a lower boiling, good solvent for the polymer and the other of which is of a higher boiling point and is a non-solvent or at least a poor solvent for the polymer. Such a polymer solution is then coated on the substrate, and dried under controlled conditions. The lower boiling solvent evaporates more readily and the coating can become enriched in the liquid which is a poor solvent or non-solvent. As evaporation proceeds, under proper conditions, the polymer formed is an isotropically porous layer. Many different polymers can be used, singly or in combination, for preparing isotropically porous "blush" polymer spreading layers for use in this invention, typical examples being polycarbonates, polyamides, polyurethanes and cellulose esters such as cellulose acetate.

A wide range of materials are useful as the spreading layer. Usually, however, materials that are resistant to, i.e., substantially non-swellable upon contact with, the liquid under analysis are desired. Swelling of about 10–40% of the layer's dry thickness may be normal.

Furthermore, although it may be possible to obtain useful spreading layers having isotropic porosity, etc., it is preferred that the material of the spreading layer be substantially non-fibrous to avoid wicking effects which tend to produce apparent non-uniform distributions of analyte between and along fibers and mottle when spreading layers of fibrous material are used as the background or milieu of spectrophotometric measurements.

The Reagent Layer(s)

Reagent layer(s) in the elements of this invention are desirably permeable, preferably uniformly permeable, and optionally porous if appropriate, to components spreadable within the metering or spreading layer. As used herein the term permeability includes permeability arising from porosity, ability to swell or any other characteristic. Such layers generally include a matrix in which is distributed, i.e., dissolved or dispersed, the enzymes and other reagents interactive with (ascorbic acid decomposition products of ascorbic acid. Interactive materials are discussed hereinafter.) Layers which serve merely as a sump for receiving a detectable species are referred to herein as registration layers.

The distribution of interactive materials (i.e., enzymes and other reagents) can be obtained by dissolving or dispersing them in the matrix material. Although uniform distributions of interactive materials are often preferred, they may not be necessary because the ascorbic acid oxidase is not consumed in any reaction but serves only as a catalyst which is continuously reused.

Desirably, reagent layers are uniformly permeable to spread components. Uniform permeability of a layer refers to permeability such that, when a homogeneous fluid is provided uniformly to a surface of the layer, measurements of the concentration of such fluid within the layer, made with identical equipment and under identical conditions but through different regions of a surface of the layer, will yield (i.e., be capable of yielding) substantially equal results. By virtue of uniform permeability, undesirable concentration gradients within, for example, a reagent layer as described herein, are avoided.

The choice of a matrix material for the reagent or registration layers described herein is, of course, variable and dependent on the intended method of use of the element as well as the particular interactive materials which are incorporated therein as described hereinafter. Desirable matrix materials can include hydrophilic materials including both naturally occurring substances like gelatin, gelatin derivatives, hydrophilic cellulose derivatives, polysaccharides such as dextran, gum arabic, agarose and the like, and also synthetic substances such as water-soluble polyvinyl compounds like poly(vinyl alcohol) and poly(vinyl pyrrolidone), acrylamide polymers, etc. Organophilic materials such as cellulose esters and the like can also be useful, and the choice of materials in any instance will reflect the use parameters for any particular element. To enhance permeability of the reagent layer, if not initially porous, it is often useful to use a matrix material that is moderately swellable in the solvent or dispersion medium of liquid under analysis.

In addition to its permeability, the reagent layer is desirably substantially free from any characteristic that might appear as or contribute to mottle or other noise in the detection of an analytical result produced in an integral element of the invention. For example, variations in color or in texture within the reagent layer, as may occur when fibrous materials such as papers are used as a permeable medium, may be disadvantageous due to non-uniform reflectance or transmittance of detecting energy, e.g., when the detectable change has occurred in and is detected in the reagent layer. Also, although fibrous materials like filter and other papers are highly permeable overall, they typically exhibit widely ranging degrees of permeability between regions of the paper, for example, based on structural variations such as fiber dimensions and spacing. As a result, such materials are not considered uniformly permeable and, as such, although useful, are not preferred in either the spreading or reagent layers of the present invention. In various preferred embodiments the spreading and reagent layers of elements absorbed herein are prepared using non-fibrous materials. It should be appreciated that the use of fibrous constituents, such as in appropriate combination with the non-fibrous materials, may be desirable.

A generally useful range of concentration for the ascorbic acid oxidase preparation in the elements of this invention is between about 0.10 and about 0.60 g/m$^2$. Indicators such as o-phenylenediamine are generally included at levels of from about 0.01 to about 1.0 g/m$^2$.

Supports

The integral analytical elements of the present invention can be self-supporting or the spreading layer, reagent layer and any other associated layers can be coated on a support. Useful support materials, when such are used, include paper and polyolefin coated paper, as well as a variety of polymeric materials such as cellulose acetate, poly(ethylene terephthalate), polycarbonates and polyvinyl compounds such as polystyrenes, etc. The support can be opaque or it can transmit light or other energy depending, of course, on the mode of detection used. A support of choice in any case will be compatible with the intended mode of result detection. Preferred supports include transparent support materials capable of transmitting electromagnetic radiation of a wavelength within the region between about 200 nm and about 900 nm. Transparent supports need not, of course, transmit over the entire 200–900 nm region but may transmit only in the region of the indicating radiation. When an element includes a support, the reagent layer is interposed in the element between the support and the spreading layer. Specifically preferred transmission ranges for elements of the present invention will be apparent from the discussion of the various preferred indicator compositions discussed above. When used, supports having thicknesses of between about 1 and about 10 mils have been found satisfactory, although the thickness can vary broadly depending on such factors, for example, as the intensity of the detecting radiation and the sensitivity of the detecting apparatus.

Other Layers

In a preferred embodiment, analytical elements of the present invention are adapted for use in analytical procedures employing reflection techniques of spectrophotometric analysis. In accordance with this embodiment, such elements will generally include a reflecting layer to provide a suitable background for spectrophotometric measurement of colorimetric or other indicator reactions. If a support is used, measurement will usually be made through the support. The reflecting layer permits the passage of ascorbic acid and/or decomposition products of ascorbic acid to the reagent or indicator layer (i.e., a layer underlying a reagent layer containing ascorbic acid oxidase which catalyzes the decomposition of ascorbic acid and only contains material which interacts with dehydroascorbic acid to produce a detectable product) and should provide an effective background for reflection spectrophotometry. A white background is generally preferred for this purpose. In view of its function as a background for indicator formed in the reagent or indicator layer, any reflective layer will normally intervene the spreading and reagent or registration layers. Such a layer may, however, intervene a reagent and indicator layer where such structure is appropriate. Reflectance can be provided by a layer also serving, for example, as a spreading layer or it can be provided by an additional layer that may not have an additional function within the element. Pigments, such as titanium dioxide and barium sulfate, are reflective and can be used to advantage in a reflecting layer. Blush polymers can also constitute a suitable reflecting material. As can be appreciated, pigment spreading layers may be useful for this purpose as can blush polymer layers that may also be spreading layers. In one preferred aspect, blush polymer layers can also incorporate a pigment to enhance spreading and/or reflectivity. The amount of pigment that can be included in a layer together with blush polymer is highly variable, and amounts of from about 1 to about 10 parts by weight of pigment per part by weight of blush polymer are preferred, with from about 3 to about 6 parts pigment per part of blush polymer being most preferred.

Filtering layers may also be present in the element. The composition and preparation of such layers are well known in the art and, when present, they serve to remove from the sample, components which could interfere with the indicating reaction or otherwise hinder the determination. Thus, in the use of the multilayer analytical element for analysis of ascorbate in whole blood, a separate filtering layer could serve to remove red blood cells while transmitting the serum to the layer below. In the analysis of blood serum or other fluids, the filtering layer may serve to remove unwanted components which could hinder or confuse the primary indicating reaction. The aforementioned blush polymer layers may also, under certain circumstances, serve as filtering layers. If the element is to be used for analysis of whole blood, it is desirable that any filtering layer have a pore size of from about 0.5 to about 5 microns.

Element Preparation

In preparing integral analytical elements of this invention, the layers can be preformed separately and laminated to form the overall element. Layers prepared in such a manner are typically coated from solution or dispersion on a surface from which the dried layer can be physically stripped. However, a convenient method which can avoid the necessity for multiple stripping and lamination steps is to coat an initial layer on a stripping surface or a support, as desired, and thereafter to coat successive layers directly on those coated previously. Such coating can be accomplished by hand, using a blade coating device or by machine, using techniques such as dip or bead coating. If machine coating techniques are used, it is often possible to coat adjacent layers simultaneously, using hopper coating techniques well known in the preparation of light-sensitive photographic films and papers. Interlayer adhesion problems can be overcome without harmful effect by means of surface treatments including extremely thin application(s) of subbing materials such as are used in photographic films.

According to one embodiment of the present invention, wherein the spreading layer performs the functions of filtering and spreading, this layer is advantageously prepared by simultaneously coating two strata of a binder such as cellulose acetate dissolved in a mixed organic solvent to provide "blush" polymer layers as described below. Such a technique simplifies the manufacturing operation by reducing the multiple coating of multiple layers to a single multiple coating operation while providing a highly useful spreading and/or filtering layer. Optionally, if desired, either or both of the discrete layers may contain dispersed therein a reflective pigment such as $TiO_2$.

The physical structure of layers prepared in this fashion generally consists of an isotropically porous upper layer which functions primarily as a metering or spreading layer to provide a uniform apparent concentration of analyte to an underlying layer in spite of variations in volume of sample applied (as described above), and a porous underlayer which functions primarily as a filter layer. The porosity of these two strata is controlled during manufacture by the use of different ratios of mixed organic solvents as described in British Pat. No. 134,228 or in the discussion of "blush" polymer layers hereinabove. A particularly useful combination of solvents when cellulose acetate is used as the binder comprises acetone, xylene and dichloroethane in ratios of from about 3.5:2:1.1 to 4.5:1:0.

The thickness of the spreading layer is variable and will depend in part on the intended sample volume, which for convenience and cleanliness the spreading layer should be able to absorb, and on the layer's void volume, which also affects the amount of sample that can be absorbed into the layer. Spreading layers having a thickness of from about 50 microns to about 300 microns have been particularly useful, although wider variations in thickness are acceptable and may be desirable for particular elements.

When preparing an isotropically porous spreading layer, it is useful to have void volume comprise at least about 25% of the total layer volume, and void volumes of from 50–95% may be desirable. Variations in void volume of porous spreading layers can be used advantageously to modify element characteristics such as total permeability of the spreading layer or the time needed for sample spreading to occur. As can be appreciated, void volume within the layer can be controlled, for example, by selecting particulate materials of appropriate size, or by varying the solvents or drying conditions when isotropically porous "blush" polymers are used in the spreading layer. The void volume of any such layer can be calculated with reasonable accuracy by a variety of techniques such as the statistical method.

The following examples will serve to further illustrate the successful practice of the instant invention.

EXAMPLE 1

Mixtures were prepared containing 10–12 $\mu$g of squash ascorbate oxidase prepared as described above and o-phenylenediamine at a level of $5 \times 10^{-3}$ M. Ascorbate was added to these mixtures at varying levels immediately after formulation and the reaction at 20°±2° C. monitored by following the increase in absorbance at 350 m$\mu$. As shown in FIG. 1, the five minute, endpoint color changes demonstrate a linear response in the ascorbate range of 0–10 mg/dl which encompasses the known normal (0.5–1.5 mg/dl) and abnormal (1.4–2.8 mg/dl) ranges in human serum. Similarly, such materials may be incorporated into any of the various "web-form" analytical elements of the prior art using conventional lyophilization or drying techniques to obtain the enzyme in dry form and for incorporating the other reagents.

EXAMPLE 2

Analytical Element for Ascorbic Acid Determination

A multilayered element for the detection of ascorbic acid was prepared as follows:

a 10 mil thick cellulose acetate support was first coated with an indicator layer comprising; gelatin (10.7 g/m$^2$), sodium phosphate buffer (pH 6.0) and o-phenylenediamine (0.10 g/m$^2$). After drying this layer was overcoated with a reagent layer comprising gelatin (5.4 g/m$^2$), sodium phosphate buffer (pH 6.8), bis (vinylsulfonylmethyl) ether (0.06 g/m$^2$), oleic ether of polyethylene glycol (0.3 g/m$^2$) and ascorbic acid oxidase (0.6 g/m$^2$). This layer in turn was coated with a spreading layer comprising microcrystalline cellulose (86 g/m$^2$) (commercial product available from FMC Corporation under the name Avicel) and polyvinylpyrralidone (2.2 g/m$^2$) in a water/isopropyl alcohol solvent mixture.

This element was evaluated by applying 10 μl aliquots of freshly prepared samples of aqueous ascorbic acid solution (0–5 mg/dl) in 0.05 M phosphate buffer at pH 6.8 to the spreading layer. The change in relative fluorescene as a function of Δmv was monitored at 340 mμ excitation and 400–600 mμ emission. The results of this testing are shown in Table III.

Table III

| Fluorometric; 3-minute end-point | |
|---|---|
| Ascorbic Acid Concentration mg/dl | Δmv |
| 0 | 0 |
| 1 | 26 |
| 2 | 54 |
| 3 | 73 |
| 5 | 122 |

The results show that the element is useful for determining the concentration of ascorbic acid in an aqueous sample only three minutes after application of the sample.

The invention has been described in detail with particular reference to certain preferred embodiments thereof, but it will be understood that variations and modifications can be effected within the spirit and scope of the invention.

It is claimed:

1. A composition for the detection of ascorbic acid comprising a dry mixture of sufficient ascorbic acid oxidase, coupling substance and buffer as to provide upon addition of water an aqueous composition buffered to a pH of between about 5.7 and about 8.7 and comprising at least about 10 μg/ml of ascorbic acid oxidase, and from about $5 \times 10^{-3}$ to about $10^{-2}$ M coupling substance which interacts with dehydroascorbic acid to produce a detectable product.

2. The composition of claim 1 wherein the ascorbic acid oxidase is from *Cucurbita pepo medullosa*.

3. An aqueous composition as described in claim 1 wherein the coupling substance is an o-, m- or p-phenylenediamine.

4. An aqueous composition for the detection of ascorbic acid, said compostion being buffered to a pH of between about 5.7 and about 8.7 and comprising at least about 10 μg/ml of ascorbic acid oxidase and from about $5 \times 10^{-3}$ to about $10^{-2}$ M of a coupling substance which interacts with dedydroascorbic acid to produce a detectable product.

5. An aqueous composition as described in claim 4 buffered to a pH of between about 6.8 and 7.2.

6. An aqueous composition as described in claim 4 wherein the ascorbate oxidase is from *Cucurbita pepo medullosa*.

7. An aqueous composition as described in claim 4 wherein the coupling substance is a o-, m- or p-phenylenediamine.

8. An aqueous composition for the detection of ascorbic acid comprising at least about 10 μg/ml of ascorbic acid oxidase, an o-, m- or p-phenylenediamine in a concentration of from about $5 \times 10^{-3}$ to about $10^{-2}$ M and buffer, said composition having a pH of between about 6.8 and about 7.2.

9. An element for the detection of ascorbic acid comprising a spreading layer and a reagent layer in fluid contact under conditions of use and containing ascorbic acid oxidase at a concentration of between about 0.10 and about 0.60 g/m$^2$ and a coupling substance at a concentration of between about 0.01 and about 1.0 g/m$^2$ which interacts with dehydroascorbic acid to produce a detectable product.

10. The element of claim 9 wherein the ascorbic acid oxidase is from *Cucurbita pepo medullosa*.

11. The element of claim 9 wherein the coupling substance is an o-, m- or p-phenylenediamine.

12. An element for the detection of ascorbic acid in a liquid, the element comprising a spreading layer, a reagent layer and an indicator layer all in fluid contact under conditions of use and a support, the reagent layer intervening the spreading layer and the indicator layer and the indicator layer intervening the reagent layer and the support, the reagent layer containing ascorbic acid oxidase at a concentration of between about 0.10 and about 0.60 g/m$^2$ and the indicator layer containing o-phenylenediamine at a concentration of between about 0.01 and about 1.0 g/m$^2$.

13. An element for the detection of ascorbic acid in a liquid, the element comprising a spreading layer, a reagent layer and an indicator layer all in fluid contact under conditions of use, the reagent layer comprising ascorbic acid oxidase at a concentration of between about 0.10 and about 0.60 g/m$^2$ and the indicator layer comprising a coupling substance at a concentration of between about 0.01 and about 1.0 g/m$^2$ which interacts with dehydroascorbic acid to produce a detectable product.

14. The element of claim 13 wherein the layer containing said ascorbic acid oxidase is buffered to a pH of between about 5.7 and about 8.7.

15. A method for detecting ascorbic acid comprising the steps of:
(a) contacting in an aqueous medium a sample for analysis and a composition buffered to a pH of betwen about 5.7 and about 8.7 and comprising at least about 10 μg/ml of ascorbic acid oxidase and from about $5 \times 10^{-3}$ to about $10^{-2}$ M of a coupling substance which interacts with dehydroascorbic acid to produce a detectable product and
(b) detecting the detectable product.

16. The method of claim 15 wherein said contacting is performed at a temperature of between about 16° and about 40° C.

17. The method of claim 15 wherein the ascorbic acid oxidase is from *Cucurbita pepo medullosa*.

18. The method of claim 16 wherein the coupling substance is an o-, m- or p-phenylenediamine.

19. The method of claim 17 wherein the aqueous medium is buffered to a pH of between about 6.8 and 7.2.

* * * * *